United States Patent
Krysiak et al.

(10) Patent No.: US 10,544,364 B2
(45) Date of Patent: *Jan. 28, 2020

(54) SOIL STABILIZER CARRIER

(71) Applicant: SKYLINE ENCAP HOLDINGS, LLC, Green Bay, WI (US)

(72) Inventors: Michael Dennis Krysiak, Green Bay, WI (US); Daniel Paul Madigan, Green Bay, WI (US)

(*) Notice: Subject to any disclaimer, the term of this patent is extended or adjusted under 35 U.S.C. 154(b) by 35 days.

This patent is subject to a terminal disclaimer.

(21) Appl. No.: 15/217,338

(22) Filed: Jul. 22, 2016

(65) Prior Publication Data

US 2016/0340582 A1    Nov. 24, 2016

Related U.S. Application Data

(63) Continuation of application No. 13/694,029, filed on Oct. 22, 2012, now Pat. No. 9,441,340, and a continuation-in-part of application No. 12/930,368, filed on Jan. 5, 2011, now Pat. No. 8,316,580, and a continuation-in-part of application No. 12/660,804, filed on Mar. 4, 2010, now Pat. No. 7,874,101, and a continuation-in-part of application No. 10/686,241, filed on Oct. 15, 2003, now Pat. No. 7,730,662, and a continuation-in-part of application No. 10/271,072, filed on Oct. 15, 2002, now Pat. No. 7,503,143.

(51) Int. Cl.

| | |
|---|---|
| C09K 17/22 | (2006.01) |
| E02D 3/12 | (2006.01) |
| A01C 1/06 | (2006.01) |
| A01N 25/14 | (2006.01) |
| C05B 7/00 | (2006.01) |
| C05B 17/00 | (2006.01) |
| C05G 3/00 | (2006.01) |
| C05G 3/04 | (2006.01) |
| C09K 17/52 | (2006.01) |

(52) U.S. Cl.
CPC ............... *C09K 17/22* (2013.01); *A01C 1/06* (2013.01); *A01N 25/14* (2013.01); *C05B 7/00* (2013.01); *C05B 17/00* (2013.01); *C05G 3/0058* (2013.01); *C05G 3/04* (2013.01); *C09K 17/52* (2013.01); *E02D 3/12* (2013.01); *E02D 2300/0082* (2013.01)

(58) Field of Classification Search
CPC ....... A01G 7/00; A01G 13/0262; C05F 11/00; C09K 17/52; C09K 17/22; C05D 9/00
USPC ........... 47/58.1 SC, 58.1 R, 9; 405/263, 264; 523/132

See application file for complete search history.

(56) References Cited

U.S. PATENT DOCUMENTS

| | | |
|---|---|---|
| 2,625,529 A | 1/1953 | Hedrick |
| 6,349,499 B1 | 2/2002 | Spittle |
| 6,395,051 B1 | 5/2002 | Arnold |
| 6,562,882 B2 | 5/2003 | Harrison |
| 6,829,860 B1 | 12/2004 | Lee |
| 6,835,761 B2 | 12/2004 | Harrison |

OTHER PUBLICATIONS

Control No. 95/001,963.
Control No. 95/001,964.
Control No. 95/001,965.
Green et al., Polyacdrylamide: A Review of the Use, Effectiveness, and Cost of a Soil Erosion Control Amendment, pp. 384-389.
LSC Environmental Products, LLC's Answer and Counterclaims in *Syline Encap Holdings, LLC* v. *LSC Environmental Products, LLC*, Civil Action No. 19-cv-280-MN (U.S. District Court for the District of Delaware), Doc. 12, filed Apr. 15, 2019 (202 pages).

*Primary Examiner* — Trinh T Nguyen
(74) *Attorney, Agent, or Firm* — Weiss & Weiss Attorneys; Philip M. Weiss

(57) ABSTRACT

A method for applying a water soluble soil stabilizer to soil wherein the soil stabilizer is added to a solid carrier.

18 Claims, No Drawings

SOIL STABILIZER CARRIER

RELATED APPLICATIONS

The present application is a continuation of application Ser. No. 13/694,029 filed on Oct. 22, 2012, which is a continuation of U.S. Pat. No. 8,316,580 issued Nov. 27, 2012 which is a continuation-in-part of U.S. Pat. No. 7,874, 101 filed Jan. 25, 2011 which is a continuation of U.S. Pat. No. 7,730,662, issued Jun. 8, 2010 which is a continuation-in-part of U.S. Pat. No. 7,503,143, issued Mar. 17, 2009.

FIELD OF THE INVENTION

A method for applying a water soluble soil stabilizer to soil wherein the soil stabilizer is added to a solid carrier.

BACKGROUND OF THE INVENTION

Water soluble polyacrylamides (PAMs) have been proposed as soil amendments for various agricultural purposes. Water soluble polymers, generically described as polyacrylamides (PAMs) appear to have a variety of beneficial soil amendment properties, including minimization of water run-off, erosion, and crusting, stabilization of soil structure, and binding of nutrients and microbes within soil.

Since the late 1980's there has been renewed interest in the use of water soluble polymers for soil physical improvement. Although PAM has been used for soil structure improvement since the 1940's and in agriculture since the 1950's the kinds of PAM used and the methods of application were different. Early PAMs had lower molecular weights than today's PAMs. They were applied to the soil at high rates, and were incorporated into the top soil by tillage.

In addition to the current interest in anionic PAMs as soil conditioners, they are widely used for other applications. PAMs are used for mineral and coal processing, petroleum production, paper making, water treating, food processing, and other miscellaneous applications.

Polyacrylamide is a synthetic water-soluble polymer made from monomers of acrylamide. It binds soil particles in the water and irrigated furrow together, making particles larger so the water has a harder time washing them out of the field.

Polyacrylamides are compounds that hold on to nutrients and troublesome microbes before they can escape from soil and make their way to ponds, lakes, streams, rivers, and/or ground water. PAM has been shown to help keep nutrients, such as nitrogen and phosphorous in fertilizers, from traveling beyond the farm in irrigation runoff. Similarly, PAM helps keep disease causing microbes, like those in cow, pig, or fish manure, from being swept beyond the confines of farmyards or feedlots.

PAM's three most common forms are dry granules, solid blocks (cubes) and emulsified liquids. The application method of PAM chosen depends on the form of PAM selected.

The use of dry granular PAM into irrigation water requires the use of an augured metering system and excellent mixing and thorough dissolving before the PAM reaches the irrigated furrows. Dry granules of PAM can be applied either by dissolving directly in the irrigation ditch before it hits the furrow, or applied directly in the furrow using what is known as the "patch method". The patch method involves placing PAM at the point in the furrow where the water first hits; applying it for a length of about 3-5 feet down the furrow to reduce the risk of the PAM becoming buried in the furrow or washing down the furrow with little to no effect. The patch method creates a sort of gel-slab at the top of the furrow where the water slowly dissolves the PAM and carries it down the furrow.

In order for the PAM to dissolve into a liquid properly in the irrigation ditch it must have proper agitation. Unlike sugar or salt which dissolve fairly quick in water, granular PAM needs to be agitated thoroughly in order for it to dissolve. If not agitated, PAM globules form, and in time the globules can float down the furrow with little effect on the furrow erosion. A way to make sure the applied PAM is dissolved is to have a drop structure in the ditch to add turbulence to the water before it hits the furrow. Another tip to achieve desired dissolving is to apply it close to the point where the irrigation water first hits the ditch. In a concrete ditch, tins or boards will provide sufficient turbulence. In an earthen ditch a drop dam works nicely.

There are many known problems for applying PAM to the soil using present applications. The dry formulation is easy to handle, but must be kept dry due to its affinity for moisture. The dry material is primarily used for open ditch application due to the difficulty of getting the material into a water pipeline. For best results, the applicators used to dispense the bulk material are placed upstream of the irrigation set and away from any splashing water droplets.

When exposed to humidity, polyacrylamide granules tend to stick to each other and to drop tubes which can then plug. The flow rate for granular PAM ranges from 2 to 33 grams per minute depending on irrigation flow and desired concentration in the irrigation water. A small error in the rate of metered PAM will lead to large differences in concentration in irrigation inflow water. Dry PAM applicator considerations include: dispensing rates of 1 to 35 grams/min; precalibrated or easily calibrated for fast setup in the field; portability; lasting power supply.

With a closed pipe system, the liquid formulation is normally recommended. Using an injector pump, the liquid can be pumped directly into the irrigation pipeline. Turbulence in the pipeline, such as an elbow, helps mix the PAM with the water. The natural turbulence in a pipeline 100 feet long or greater is likely sufficient for mixing. The liquid material is, however, difficult to handle outside of the container. To clean up anything that has come in contact with liquid PAM, it is common practice to "wash" the PAM off with soil. The PAM will adhere to the soil particles making cleanup with water possible.

The liquid formulation also can be used for open ditch applications; however, if a pump is not being used, and the liquid dribbles into the water, the viscosity of the liquid can change with temperature changing the calibrated delivery rate. Keeping the containers out of direct sunlight will reduce, but not eliminate, this problem.

Liquid PAM can be metered directly from the container into the irrigation ditch, directly into the furrow, or through a pipe line or injector pump. Emulsified PAM (special liquid PAM solutions) can be applied like the granular form into irrigation ditches or into furrows using the patch method. Emulsified PAM doesn't require quite the vigorous mixing as the granular form, but still needs adequate mixing for dissolving. Emulsified PAM is more voluminous than dry forms, but has an easier time dissolving and is the only form of PAM that should be used for sprinkler irrigating systems, due to greatly reduced the risk of clogging the lines.

The solid formulation of PAM is placed in an area where turbulence is occurring. The action of the water slowly dissolves the polyacrylamide into the flowing water. The only way to control the amount added into the water is to control where the solid PAM is placed and how long it is left in the water. Calibration for dispersion rate has not yet been determined, so trial and error is the current method used.

PAM blocks (or cubes) are usually placed in wire baskets in flowing ditches at turbulent points. The wire baskets need to be secured to the edge of the ditch to avoid washing of the blocks down the ditch. The blocks slowly dissolve, releasing small amounts of PAM into the water. Of the three forms PAM blocks may not perform as well as liquid or granular PAM in furrow irrigation. PAM blocks, however, have been useful for treating settling ponds to accelerate water clarification and promote flocculation. They can also be used to dose concentrated runoff areas on fields that otherwise cause uncontrolled erosion.

Adding polyacrylamide to water is much different than adding most other materials. For example, if a cup of salt water is added to a gallon of water and stirred, the salt will, in a short period of time, dissolve. However, when polyacrylamide is added to water, turbulence is necessary to ensure adequate mixing. Without adequate mixing, the polyacrylamide will not immediately dissolve and PAM globules will form. In time, these globules will find their way to the field and can be seen floating down the furrow. Although not as likely, globules do still occur with injector system use. If PAM is being applied with a center pivot, sprinkler nozzle, plugging may occur if the PAM solution is not well mixed.

The application method depends on the material selected. Granular PAM requires some form of augured metering system. Solid blocks should be placed in a wire basket and secured to the side of the ditch to avoid washing the block downstream. Liquid PAM can be metered directly from the container into an open ditch or through an injector pump into a pipeline.

If adding either liquid or dry PAM to an open ditch, the discharge point is kept at least 2 feet away from the flowing water. Small droplets of water can cause the PAM to clog at the outlet and stop flow. If turbulence in the water is causing splashing, the applicator is moved away so that the water does not contact the container or move the turbulent flow downstream.

Another concern, is the type of water used for irrigation. Because polyacrylamide attaches to the soil particles and binds them together, water containing a lot of sediment may result in sediment settling out before water is diverted into the furrows. In general, this does not affect PAM's effectiveness, but with extremely sediment-laden ditch water, sediment may build up and restrict flow in the supply ditch. This is also a concern for underground transport pipes. If the water velocity in the pipe is insufficient to lift the accumulated sediment, pipe flow may be restricted. Though the pipe flow rate is reduced, the pipe is not likely to plug completely, since as the sediment decreases the pipe's inside diameter, water velocity increases.

Different soil textures and field slopes can give different results when receiving equal quantities of PAM. One can start with the 10 ppm rate and increase or decrease the concentration based on the clarity of the runoff leaving the field.

For maximum effectiveness, thoroughly mix PAM with the irrigation water before application. In an open ditch, let the water pass over at least one drop structure or some ditch obstruction to cause turbulence before water is diverted into the furrows. In an earthen ditch, a drop dam will suffice; in a concrete ditch, boards can be used to create the turbulence. In some cases a drop is created in order to adequately mix the material in water. In gated pipe, the pipe swirling action will generally cause enough mixing within the first 2-3 pipe joints. If pressure in gated pipe is relatively low, 3 feet or less, a Krause Box can be used to create a drop structure in the pipeline.

Regardless of what form of PAM is supplied to the farmers (dry material, concentrated material, or pre-mixed stock solution) it is important to provide aggressive mixing (agitation) at the point of application of PAM to the water sources. The agitation requirement increases as the concentration of stock solution increases and is greatest for use of direct dry PAM application. Agitation should be provided by use of a stream drop and multiple flow obstructions near the point of injection. With vigorous turbulent flow 25-50 ft of ditch canal should be allowed for stock solution mixing before the first siphon tube withdrawal or gate. Dry PAM may need longer ditch runs for adequate mixing. If using gated pipe, the first length of gated pipe after the point of PAM injection should have one or two baffles to enhance mixing. PAM should not be added upstream from weed screens or filters of any kind. Heating of water of stock solution greatly enhances PAM dissolution and mixing.

The furrow is considered treated once the water reaches the end of the field, and additional polymer is normally not required for that irrigation. In many cases, producers have found that, rather than applying PAM until water advances to the end of the field, protection is adequate by applying PAM only until water advances 50 percent or less of the field length. The advantages are erosion control in the top portion of a field, reduction of sediment deposits in the bottom portion of the field and reduced application costs.

Because polyacrylamide attaches itself to the soil near the surface, cultivation or ditching after PAM application results in loss of effectiveness. PAM should be reapplied after cultivation or ditching disturbs the soil surface. Once applied, PAM is not effective all season long. However, after the initial application, PAM does continue to offer some erosion control during subsequent irrigations. Factors, such as soil type, field slope and irrigation furrow stream size, will determine the long-term effectiveness of a single PAM application.

Inadequate mixing of PAM may result in highly concentrated PAM being applied in the first few furrows and insufficient PAM in the furrows furthest from the point of injection.

The use of automated timers or liquid shutoff valves can be problematic for controlling PAM injection because it is difficult to accurately predict furrow advance time. If advance time is slower than expected, the bottom portion of the fields will not be treated with PAM. If furrow advance is faster than expected more PAM than necessary will be applied and PAM losses in runoff water could occur.

If using PAM in sprinkler irrigation, the pipes must be pressurized to be sure water is delivered before injecting PAM into the flow. This protocol assures that PAM does not build up in sprinkler lines before water enters the pipes (which would violate the caution of not adding water to PAM). Benefits of using PAM with sprinkler irrigation are much less dramatic than with furrow irrigation. Applying 2-4 lb PAM per acre can reduce erosion and increase infiltration during the irrigation under some conditions. However, beneficial effects last for only one or two irrigations.

PAM treatment has usually been by injection of small amounts of concentrated stock solutions into the irrigation water supply. There is some indication that direct powder addition may be feasible, but the concept has not been extensively tested. PAMs are applied via irrigation water to only that small part of the soil that play a role in the physical processes of erosion, sealing and crust formation.

Water-applied PAM increases soil cohesion and strengthens the aggregates it contacts in the furrow by binding exposed soil particles together more securely. This greatly reduces detachment and transport of sediments in irrigation runoff. Soil erodibility at the soil water interface is reduced by improved inter-aggregate bonding and better maintenance of surface roughness. PAM also acts as a settling agent. It flocculates (clumps together) the fine particles. If an irrigation is not adjusted, over-wetting of the upper and/or underwatering of the lower ends could be worsened.

Most states require that agricultural chemicals (including soil amendments such as PAM) meet safety and state labeling requirements. The PAMs currently labeled are water soluble, anionic (11-20%), high (10-15 million) molecular weight compounds meeting EPA and FDA monomer limits below 0.05%. PAM is available in several forms: dry powder or granules containing 80-95% active ingredient (AI); inverse oil-emersion liquid concentrates containing 30-50% AI (PAM is dissolved in water droplets that float in an oil matrix); and pre-mixed PAM-water solutions containing <3% PAM.

At a minimum PAM should be used on the first irrigation and when soil is disturbed by traffic and/or cultivation. Additional applications at or below label amounts may be considered to provide complete erosion control for the entire season. If PAM is applied in the first irrigation and subsequent irrigations have no PAM in the water, then erosion control and infiltration effects can be expected to decline approximately 50% with each non-treated irrigation. Thus, by the third irrigation, little effect remains. For those crops in which erosion naturally subsides during mid season, PAM need not be applied after the natural erosion reducing properties ensue.

Polyacrylamide (PAM) is a long-chain molecule commonly used to clean waste water. To date, the primary market for this compound has been municipal wastewater treatment facilities. It makes the fine solids in treated water glom onto one another, until they become big enough to settle out or be captured by filters to make sewage sludge.

PAM seeks out and binds to the broken edges of clay particles, which carry a negative charge. By increasing the cohesiveness of soil particles on the soil surface of a field, PAM makes dirt more resistant to the highly erosive shear forces exerted by water flowing over it. This binding is referred to as flocculation. Flocculation is used to describe the action of polymeric materials which form bridges between individual particles. Bridging occurs when segments of a polymer chain adsorb on different particles and help particles aggregate. Flocculants carry active groups with a charge which will counterbalance the charge of the particles. Flocculants adsorb on particles and cause destabilization either by bridging or charge neutralization. An anionic flocculant will usually react against a positively charged suspension (positive zeta potential). That is the case of salts and metallic hydroxides. A cationic flocculant will react against a negatively charged suspension (negative zeta potential) like silica or organic substances.

The most common polymers are those based on polyacrylamide, which is a nonionic polymer. Their effect is due to bridging between particles by polymer chains. Polymers can be given anionic character by copolymerizing acrylamide with acrylic acid. Cationic polymers are prepared by copolymerizing acrylamide with a cationic monomer. All available acrylamide based polymers have a specific amount of ionic monomer giving a certain degree of ionic character. They have a specific average molecular weight (i.e. chain length) and a given molecular distribution. For each suspension, a certain degree of anionic, cationic or nonionic character is beneficial. Usually, the intrinsic flocculating power increases with the molecular weight. Polyacrylamides have the highest molecular weight among the synthesized industrial chemicals in the range of 10-20 millions. Other polymers display specific properties and are used under specific conditions. They are mostly: Polyethylene-imines, polyamides-amines, polyamines, polyethylene-oxide, sulfonated compounds.

Anionic PAM are "Off the Shelf" Industrial Flocculants used extensively for: potable water treatment, dewatering of sewage sludges, washing and lye-peeling of fruits and vegetables, clarification of sugar juice and liquor, adhesives and paper in contact with food, animal feed thickeners and suspending agents, cosmetics, paper manufacturing and various mining and drilling applications.

U.S. Pat. No. 6,357,176 relates to a soil and grass seedless sod precursor containing a non-woven bio-cellulosic fiber mat and grass sprigs. The sod precursor can be used to produce a soil-free sod which is useful for manufacturing athletic fields, golf courses and lawns. The mat may contain other materials in addition to the bio-cellulosic fiber. The mat may contain other types of fibers, such as wood fibers or synthetic organic fibers. Wood fibers may increase the water retention of the mat. Examples of organic fibers include acrylic, cellulose ester, elastomeric, olefin, polyester, polyamide and polyvinyl alcohol fibers. A synthetic organic polymer may function as a binder. The mat may also contain non-fibrous polymers, such as polysaccharides, proteins, polyacrylamide and other water retention agents. The prior art patent uses polyacrylamide to increase water retention of the mat.

U.S. Pat. No. 5,900,038 relates to a cultivation substrate and method of preparing the same. The cultivation substrate contains comminuted plants selected from among knot grass, C4 plants and plants of the *cannabis* and *Dicksonia* genuses, and is suited as a peat substitute. During the comminution process, or thereafter, additives may be added, depending on the later use of the cultivation substrate. Polyacrylamide granules, clay mineral mixtures, ground lava rock, pumice, bentonite, sand, waste paper, fly ash from brown-coal combustion, brown-coal waste and all kinds of fertilizers are suited as additives. Polyacrylamide granules improve the cultivation substrate of the invention in that it possesses a high water storing capacity for the mulch. Gelling cross-linked polyacrylamide granules, as are e.g., obtainable under the name Polywater-Aqua-Plus from Polyplant GmbH, Xanten, are especially advantageous. This prior art patent uses polyacrylamide to increase the water storing capacity of the mulch.

U.S. Pat. No. 4,337,117 relates to a synthetic sheet material resistant to decay by fungus and other microbial organisms and useful in shoe construction, mulch papers and the like. The material comprises a uniform distribution of cellulose and optionally synthetic fiber within a matrix or binder and is formed from a furnish of the fibers; a metallic quinolinolate which lends the material decay resistant; a polymer colloid such as an acrylic latex which prevents the coagulation of the subsequently added elastomeric binder by the metallic quinolinolate; and a cationic polymer which acts as a retaining agent for the metallic quinolinolate in the synthetic sheet material. The decay resistant sheet material is formed generally by a papermaking process. The cationic polymer can be polyacrylamide polymers. The polyacrylamide is used to make the sheet material decay resistant.

U.S. Pat. Nos. 5,429,741 and 5,641,458 relate to methods for treating sludge with processed cellulose material combined with another material, e.g., a surface active agent, a detergent, a surfactant, a polymer and/or an organic polymer. Cellulose flakes and a method for making them are disclosed. They can be used for animal litter or bedding, food or fertilizer. Methods for absorbing, removing, and for cleanup of a first liquid floating on or in a second liquid are disclosed, the method employing absorbent pellets. A typical surfactant useful in sludge conditioning includes emulsions such as polyacrylamide. This prior art reference used the PAM as a surfactant for the sludge treatment.

U.S. Pat. No. 5,456,733 relates to a process for producing novel mulching pellets from waste paper scrap by incorporating particulate water-insoluble, swellable, gel-forming polymer into the pellet-forming composition. The formed pellets swell and disintegrate after being spread and impregnated with water, to increase their area of ground coverage, to release any included nutrients or seeds, and to deposit polymer particles having water-absorbing properties.

The invention relates to a method for producing dry extruded mulching pellets, containing particulate waste paper and a swelling agent, capable of application by means of simple spreading devices and being highly water-absorbent and water retentive. Upon impregnation with applied water or rain, the pellets swell, expand and disintegrate to increase their area of ground coverage and provide a water-absorbing surface covering which prevents water run-off and which helps maintain moisture in the soil. The polyacrylamide increases water absorption of the pellets. The disintegration or coming-apart of the swollen pellets also increases the exposed surface area of the mulch and facilitates the release of seed and the release of nutrients into the soil to support germination and growth of seed and plants in the soil.

The most essential feature of the process and mulch pellets is the incorporation of a swelling agent comprising a water-insoluble, swellable, gel-forming, hydrophilic polymeric material, capable of absorbing substantial amounts of water, into pellets comprising waste paper particles. The process consists nearly entirely of particulate waste paper and contains a minor amount by weight, up to 10%, of a water soluble, film-forming, polymeric binder material, and up to 10% of a swelling agent comprising a water-insoluble, water swellable, gel-forming, hydrophobic polymeric material in particulate form, distributed throughout the pellets. The mulch pellets comprise up to about 99% by weight of particulate waste paper, which contains a small amount by weight of a water-soluble film forming binder material such as polyvinyl alcohol and/or cellulose binder material such as carboxymethyl cellulose to bind the wood fibers in the paper making process. The essential additive is the water-insoluble, gel forming, hydrophilic polymer which is uniformly mixed in a powder form. The composition is fed to a conventional pellet mill and pelletized. Examples of polymers are cross-linked polyacrylamide polymers or polyacrylate polymers. This prior art used PAM for the benefit of it's swelling ability of the pellets.

U.S. Pat. No. 6,349,499 relates to a flaked mulch product having a density similar to that of seed which is to be established, comprising an agglomerated and compacted natural raw material whose density is adjusted to within 50% of the seed. The invention provides lignocellulosic mulch product. To the raw materials may also be added various additives such as dyes and pigments, germination aids, fertilizer, and one or more surfactants and/or water absorbing substances. Surfactants may be added to encourage rapid water uptake and retention. Water absorbent materials such as polyacrylic acids, other polyacrylates, and the like may be used. In some uses, such synthetic polymers may also serve as the binder, e.g., polyacrylic acid, polyacrylamides, and various acrylate, acrylic acid, and acrylamide co-and terpolymers. This prior art reference used PAM as a binder for the mulch product.

U.S. Pat. No. 6,360,478 relates to a completely biodegradable mulch product which forms a mechanically bonded yet open fiber mulch matrix containing natural fibers and interlockable crimped natural fibers, the crimped natural fibers being crimped by a process which induces a water-resistant permanent crimp.

A polymer-based water absorbent may be dispersed throughout the fiber mulch to increase the mulch water absorption capacity. The polymer based water absorbent is preferably present at about 5% to 15% of the mulch weight. The water absorbent is preferably a powder such as a polyacrylamide-based copolymer powder that absorbs many times its own weight in water. The polymer-based water absorbent is then dispersed into the fiber mulch to increase its water absorption capacity. The water absorbent is preferably mechanically dispersed into the mixed mulch fiber-crimped synthetic fiber mulch. This prior art reference used PAM for the benefit of the mulch product.

U.S. Pat. Nos. 5,741,832, 5,779,782 and 5,942,029 relate to mechanically bonded, water absorbent fiber mulch including natural and crimped synthetic fibers that are intimately mixed to form a mechanically bonded fiber mulch. A water-absorbent polymer based material is dispersed throughout the fiber mulch to increase its water absorption capacity. The polymer based water absorbent is preferably present at about 5% to 15% of the mulch weight. The water absorbent is preferably a powder such as polyacrylamide based copolymer powder that absorbs many times its own weight in water. The polymer-based water absorbent is then dispersed into the fiber mulch to increase its water absorption capacity. The water absorption is preferably mechanically dispersed into the mixed natural fiber-synthetic fiber mulch. This prior art reference used PAM for the benefit of the mulch product.

None of the prior art references uses solid carriers as a means of applying PAM to the soil. In the prior art, PAM has been included in mulch, as a surfactant, as a water absorbent polymer, to alter the state of the mulch (cause expansion of the mulch when watered), increase mulch size to enable the mulch to better cover the seed bed, to increase the mulch's ability to absorb more water to lower the amount of excess water, and hence reduce water runoff and hence soil loss, to hold mulches together as a binder and to increase stickiness of a mulch to keep it in place.

SUMMARY OF THE INVENTION

The present invention relates to a method for applying PAM or another soil stabilizer to soil wherein PAM or another soil stabilizer is precisely intermixed, impregnated and/or applied to solid carriers. The solid carriers can be comprised of organic and/or inorganic materials that can be applied to soil. These materials may contain fertilizers, soil amendments, soil conditioners, and/or waste products. The solid carrier can be produced by agglomeration. It is an object of the present invention for the solid carrier to be an agglomerate. Other terms commonly used to describe agglomeration is granulation and compaction as they both relate to particle size enlargement. The solid carrier acts as a delivery system for the soil stabilizer. By controlling the rate of solid carrier metered to the soil, you in turn, control the amount of soil stabilizer metered to the soil. The present invention relates to any solid carrier that can be applied through conventional means, such as, spreaders. In a preferred embodiment, these industries include agricultural and horticulture. PAM is not easily applied to the soil. It is currently applied via irrigation systems or in it's dry, granular form. Given its low rate of application, challenges are many.

The present invention relates to a method of applying a water-soluble soil stabilizer to soil comprising: adding the water-soluble soil stabilizer to a solid carrier. The water-soluble soil stabilizer is released out of the solid carrier to the soil. The water-soluble soil stabilizer binds to the soil. Application rates of the solid carrier to the soil are based on desired amount of the water-soluble soil stabilizer to be metered to the soil. The solid carrier comprises a soil stabilizer.

An example of this is if the soil stabilizer is polyacrylamide and the solid carrier comprises guar, guar is also a soil stabilizer.

The present invention relates to a method of applying a water-soluble soil stabilizer to soil comprising: adding the water-soluble soil stabilizer to a solid carrier. The water-soluble soil stabilizer releases the soil stabilizer out of the solid carrier to the soil. The water-soluble soil stabilizer binds to the soil. The application rates of the solid carrier to the soil is based on desired amount of water-soluble soil stabilizer to be metered to the soil. The solid carrier comprises paper based mulch and biosolids.

The present invention relates to a method of applying a water-soluble soil stabilizer to soil comprising: bulk blending a water-soluble soil stabilizer with solid carriers. The water soluble soil stabilizer when bulk blended with the solid carriers stays substantially suspended within the solid carriers. The solid carriers and soil stabilizer are placed on the soil. The water water-soluble soil stabilizer binds to the soil.

It is an object of the present invention for the solid carriers to keep the soil stabilizer suspended substantially uniformly throughout the solid carrier while in a package. It is an object of the present invention for the solid carriers to possess interlocking properties consisting of having hook-type projections.

It is an object of the present invention for the solid carriers to be small enough to resist segregation, be asymmetrical and possess interlocking properties.

It is an object of the present invention for water to be added to the solid carriers and soil stabilizer to release the water-soluble soil stabilizer from the solid carriers.

It is an object of the present invention for the solid carriers to be comprised of: fertilizers and/or soil amendments. It is an object of the present invention for the solid carriers to comprise fibrous material.

It is an object of the present invention for the solid carriers to further comprise a seed. It is an object of the present invention for the method to further include adding pesticides, herbicides and/or insecticides to the solid carriers.

It is an object of the present invention for the solid carriers to be an agglomerate. It is an object of the present invention for the solid carriers to be in the form of a granule, extruded pellet, woven mat, flake and/or formed bale.

It is an object of the present invention for the solid carriers to further comprise aluminum sulfate and/or calcium oxide.

It is an object of the present invention for the water-soluble soil stabilizer to be selected from the group consisting of: polyacrylamide, polyethylene-imines, polyamides-amines, polyamines, polyethylene-oxide, guar, and sulfonated compounds.

It is an object of the present invention for the solid carriers to be comprised of a material that was previously treated with an ingredient that has soil stabilizing properties. It is an object of the present invention for the material to be derived from potable water treatment, dewatering of sewage sludges, washing and lye-peeling of fruits and vegetables, clarification of sugar juice and liquor, adhesives and paper in contact with food, animal feed thickeners and suspending agents, cosmetics, paper manufacturing, various mining and drilling applications.

It is an object of the present invention for the solid carriers to contain mineral elements. It is an object of the present invention for the solid carriers to comprise fibrous material, a seed, a mulch, and/or a material that was previously treated with water-soluble soil stabilizer; wherein the material includes material from mineral and coal processing, petroleum production, paper making, water treating, and food processing.

It is an object of the present invention for the solid carriers to be comprised of nitrogen, phosphorus and/or potassium.

It is an object of the present invention for the solid carriers to be an erosion control BMP such as seed and mulch or erosion mat. It is an object of the present invention for the solid carriers to be comprised of an amendment, soil conditioner and/or waste product.

It is an object of the present invention for the solid carriers to be made by a size reduction and/or an agglomeration process, including agitation, pressure, liquid and/or thermal; wherein said agitation process includes the methods of; tumbling, mixing, granulation, pelletizing, balling, conditioning, and/or instantizing; wherein said pressure process includes the methods of briquetting, compacting, extrusion, pelleting, molding, tabletting and/or isostatic pressing; wherein said liquid process includes the methods of spray drying, spray granulation, fluid bed granulation, prilling, agglomeration in liquid media, oil agglomeration and/or globulation; wherein said thermal process includes the methods of sintering, induration, nodulizing, calcining, drying/solidification, partial gasification/charring and flaking.

It is an object of the present invention for the soil stabilizer to further comprise cross-linked soil stabilizers.

It is an object of the present invention for the application rates of the solid carriers to the soil to be based on desired amount of the water-soluble soil stabilizer to be metered to the soil.

The present invention relates to a delivery system used to apply water-soluble soil stabilizer to soil comprising: solid carriers bulk blended with a water-soluble soil stabilizer; wherein the water-soluble soil stabilizer stays substantially suspended within the solid carriers.

The solid carriers reduce segregation (unmixing) tendencies of the water-soluble soil stabilizer from the solid carriers. U.S. Pat. No. 6,745,513 is incorporated for reference.

It is an object of the present invention for the solid carrier to have a non-smooth surface.

It is an object of the present invention to reduce segregation tendencies of blends of materials, including water soluble soil stabilizers. Segregation of materials can be influenced by many factors, including, particle size, bulk density, particle shape, and particle friction. It is an object of the present invention that the solid carriers have a light bulk density.

When the solid carriers are packaged with the soil stabilizer, the soil stabilizer is prone to stay suspended throughout the carrier. The composition of the invention flow freely through various spreaders. When applied, the solid carriers act as a delivery system for the soil stabilizer.

The present invention relates to adding PAM to a solid carrier, applying the solid carrier to the soil; applying water to the solid carrier; and leaching PAM out of the solid carrier into the soil. The water can be natural in the form of rain or applied by man made means. The water serves as an activation agent or catalyst in that, without it, neither component provides much value to the soil and/or plant life. It is an object of the present invention for the PAM to be in a dry granular form. It is an object of the present invention for the solid carrier to comprise a mulch or fertilizer. It is an object of the present invention to add fertilizers and/or soil amendments to the solid carrier. It is an object of the present invention for the solid carrier to comprise fibrous material. It is an object of the present invention for the solid carrier to be in the form of a granule, extruded pellet, woven mat, flake and/or formed bale and or size reduced particle. It is an object of the present invention for the solid carrier to contain a seed. It is an object of the present invention to add pesticides or herbicides to the solid carrier. It is an object of the present invention for the solid carrier to comprise a fertilizer. It is an object of the present invention for the solid carrier to have disease causing microbes, such as animal manure added to it. It is an object of the present invention for the solid carrier used to apply PAM to soil to comprise mulch and PAM. It is an object of the present invention to add aluminum sulfate and/or calcium oxide to the solid carrier. The addition of these elements with PAM assists in slowing down the loss of phosphorous in runoff.

The present invention relates to a method for applying a soil stabilizer to the soil comprising adding a soil stabilizer to a solid carrier and applying the solid carrier to the soil. Water is applied to the solid carrier which then releases the soil stabilizer out of the solid carrier into the soil. It is an object of the present invention for the soil stabilizer to be selected from the group consisting of: start xanthate, acid hydrolyzed cellulose microfibrils, chitin, gypsum, PAM, hydrocolloidal polysaccharide, acrylic copolymers, and/or sodium acrylate, and any combination of the above.

It is an object of the present invention for the weight of the soil stabilizer to be less than 50% of the total solid carrier weight.

It is an object of the present invention for the soil stabilizer to be selected from the group consisting of: polyacrylamide, polyethylene-imines, polyamides-amines, polyamines, polyethylene-oxide, and sulfonated compounds.

It is an object of the present invention for the solid carrier to be comprised of a material that was previously treated with an ingredient that has soil stabilizing properties.

It is an object of the present invention for the material to be derived from potable water treatment, dewatering of sewage sludges, washing and lye-peeling of fruits and vegetables, clarification of sugar juice and liquor, adhesives and paper in contact with food, animal feed thickeners and suspending agents, cosmetics, paper manufacturing, various mining and drilling applications.

It is an object of the present invention for the solid carriers to include mineral elements. It is an object of the present invention for the soil stabilizer to hold mineral elements in the soil. There are 13 mineral elements within the soil that are recognized as being essential for plant growth. The amounts of these elements found within plants vary considerably; hence they are grouped into macronutrients, secondary nutrients, and micronutrients, depending on the relative amounts required for growth. Macronutrients are: Nitrogen, Phosphorous and Potassium. Secondary nutrients are sulfur, calcium and magnesium. Micronutrients are iron, manganese, boron, copper, zinc, molybdenum and chlorine.

The present invention relates to a method of applying cross-linked polyacrylamide to soil comprising: adding cross-linked polyacrylamide to a solid carrier. The solid carrier is applied to the soil. Water is then applied to the solid carrier. This releases the cross-linked polyacrylamide out of the solid carrier and into the soil.

The present invention relates to a solid carrier used to apply cross-linked polyacrylamide to soil comprising a solid carrier and cross-linked polyacrylamide.

The present invention relates to a method of applying soil stabilizer to soil comprising adding soil stabilizer to a solid carrier. The solid carrier is comprised of at least 25% particles in excess of 1 mm in diameter. The solid carrier is applied to soil. Water is applied to the solid carrier releasing the soil stabilizer out of the solid carrier into the soil.

Solid carriers can be made by a number of ways of agglomeration processes, including agitation, pressure, liquid and thermal. Agitation agglomeration includes the methods: tumbling, mixing, granulation, pelletizing, balling, conditioning, and instantizing. Pressure agglomeration includes the methods: briquetting, compacting, extrusion, pelleting, molding, tabletting and isostatic pressing. Liquid agglomeration includes the methods: spray drying, spray granulation, fluid bed granulation, prilling, agglomeration in liquid media, oil agglomeration and globulation. Thermal agglomeration includes the methods: sintering, induration, nodulizing, calcining, drying/solidification, partial gasification/charring and flaking.

Agitation agglomeration can use the following equipment: mixers (planetary, cone, ribbon, pintype, drum, counter-current, vertical, paddle, pugmills), Disc pelletizers (pan granulators), drum pelletizers and cone pelletizers. Pressure agglomeration can use the following equipment: roller presses (roll briquetters, roll compactors), piston/ram presses, pellet mills (ring die, flat die), extruders (auger, screw, screen, basket), tablet presses. Liquid agglomeration can use the following equipment: spray dryers, prill towers, spray/fluid bed, granulators, mixers for oil agglomeration. Thermal agglomeration can use the following equipment: sinter strands, traveling grates, rotary kilns, shaft furnaces and drum/belt flakers.

Solid carriers can also be made via a process of size reduction wherein a material is reduced into smaller particle sizes. In an embodiment, the solid carrier is comprised of materials that are not in a liquid or slurry state.

It is an object of the present invention for the PAM to be anionic. It is an object of the present invention for the PAM to be neutral. It is an object of the present invention for the PAM to be cationic.

It is an object of the present invention for the soil stabilizer to reduce the need for erosion mats in slope applications prior to establishment of permanent vegetation. It is an object of the present invention for the PAM to increase permeability of the soil. It is an object of the present invention for the PAM to bind to the soil to increase infiltration of the fertilizer and water within the soil.

It is an object of the present invention for the soil stabilizer to improve water infiltration of the soil, thereby improving the soil's ability to absorb water. It is an object of the present invention for the soil stabilizer to improve water infiltration of the soil, thereby reducing the amount and/or frequency of water needed for the soil. It is an object of the present invention for the soil stabilizer to reduce soil packing and cracking. It is an object of the present invention for the soil stabilizer to improve soil tillability. It is an object of the present invention for the soil stabilizer to be an anti-crusting agent in the soil. It is an object of the present invention for the soil stabilizer to reduce rilling of the soil.

It is an object of the present invention for PAM to bind to the fertilizer to reduce leaching of the fertilizer within the soil. It is an object of the present invention for the PAM to bind to the soil and the fertilizer to reduce runoff of the fertilizer from the soil. It is an object of the present invention for PAM to bind to the soil and the fertilizer to hold the fertilizer in the soil. It is an object of the present invention for the soil stabilizer to reduce erosion of the soil, thereby reducing erosion of the fertilizer, thereby reducing fertilizer usage and fertilizer cost per acre. It is an object of the present invention for the soil stabilizer to improve water infiltration of the soil, thereby reducing erosion of the fertilizer, thereby reducing fertilizer usage and fertilizer cost per acre. It is an object of the present invention for the soil stabilizer to hold nutrients in the soil, thereby reducing fertilizer usage and cost per acre.

By combining plant nutrients with the proper soil conditioning materials, more of the plant nutrients can be made available for uptake by the targeted plants. Since PAM binds nutrients and stabilizes soil, it reduces fertilizer leaching and runoff. In effect it works as a PAM dam to fertilizer as it works to maximize the performance if the soil in relationship to the nutrients. PAM acts as an enabler to soil to improve its capacity to hold the nutrients in place for use by the plants.

It is an object of the present invention for the soil stabilizer to reduce runoff and leaching of microbes in the soil. It is an object of the present invention for the soil stabilizer to prevent movement of sediment containing nutrient, pesticides and other matter. It is an object of the present invention for the soil stabilizer to comprise aluminum sulfate and/or calcium oxide. It is an object of the present invention for the soil stabilizer to reduce total fecal coliform bacteria and fecal strep leaching and runoff from the soil. It is an object of the present invention for the soil stabilizer to control erosive forces by holding soils in place and ionically bonding them together to increase particle size.

It is an object of the present invention for the soil stabilizer to improve survival and growth of plants. It is an object of the present invention for the soil stabilizer to reduce the time for seed emergence within the soil. It is an object of the present invention for the soil stabilizer to improve root growth of plants within the soil. It is an object of the present invention for the soil stabilizer to improve crop yield within the soil. It is an object of the present invention for the soil stabilizer to when added to the soil to result in a cleaner harvest of root crop. It is an object of the present invention for the soil stabilizer to expedite crop maturity.

It is an object of the present invention for the soil stabilizer to increase viability of shrub, tree, and/or vegetable transplants. It is an object of the invention for the soil stabilizer to deepen plant rooting in the soil. It is an object of the present invention for the soil stabilizer to advance planting dates by drying the soil faster. It is an object of the present invention for the soil stabilizer to improve crop quality in the soil. It is an object of the present invention for the soil stabilizer to increase germination rates of the seed in the soil. It is an object of the present invention for the soil stabilizer to reduce soil-borne diseases within the soil.

The present invention relates to a method of improving soil penetration comprising; applying to the soil by conventional application equipment a solid carrier. The solid carrier comprises a soil stabilizer. Water is added to the solid carrier, releasing the soil stabilizer into the soil.

The present invention relates to a method of reducing soil erosion comprising; applying to the soil by conventional application equipment a solid carrier. The solid carrier comprises a soil stabilizer. Water is added to the solid carrier, releasing the soil stabilizer into the soil.

The present invention relates to a method of reducing fertilizer runoff and leaching comprising; applying to the soil by conventional application equipment a solid carrier. The solid carrier comprises a soil stabilizer. Water is added to the solid carrier, releasing the soil stabilizer into the soil.

Water soluble polyacrylamides (PAMs) have been proposed as soil amendments for various agricultural purposes. Water soluble polymers, generically described as polyacrylamides (PAMs) appear to have a variety of beneficial soil amendment properties, including minimization of water run-off, erosion, and crusting, and stabilization of soil structure. This benefit extends to the general reduction of runoff of fertilizer, pesticide and herbicide.

PAM is a long chain synthetic polymer that acts as a strengthening agent, binding soil particles together. It is harder for water to move these larger, heavier particles of soil. PAM applied in the irrigation water reduced soil erosion in furrows by over 95 percent, when compared to irrigation without the polymer.

The present invention allows the user to not have to mix the PAM in the field. The PAM of the present invention does not clog weed screens, filters or narrow siphons as this equipment is not required. Further the method of the present invention allows a user to avoid the risk of handling the dry concentrate. The method of the present invention further avoids the bulkier equipment that has been used to apply PAM in the prior art. The method of the present invention avoids the need for large stock solution volumes which are needed for large fields, or where advance rate is slow; mixing field solution from concentrate which takes considerable time and requires dedicated equipment.

The method of the present invention avoids the disadvantages of adding a liquid concentrate (oil-emulsion) application directly to the soil. Using the method of the present invention, application is done using standard spreading equipment and need not be sophisticated (compared to that for pre-mixed solutions) to obtain uniform metering rates. The present invention does not require oil and surfactant components that provide no known benefits to crops.

Though PAM can be incorporated in any physical state into the solid carrier under the current invention, dry PAM is preferred because it impregnates easier into the solid carrier then other forms of PAM. Also dry PAM can be purchased and stored and may be the least expensive form of PAM. Further, by applying PAM by the method of the present invention application equipment does not tend to plug, nor does weed screens and filters. There is no danger from choking from inhalation of PAM dust while filling machine. If one were to apply dry PAM directly to a field, there would be greater PAM losses from the field since there is less control of dissolution. Further by applying dry PAM directly to the soil there is poorer uniformity of distribution than the present invention. The rate of PAM addition must be based on total irrigation inflow rate, erosion potential for a field, and desired injection concentration.

Application rates of anionic PAM mixtures may need to be adjusted based on soil type, slope, and type of erosion targeted (i.e., wind or water). Anionic PAM mixtures may be applied to steeper slopes when used with other erosion control BMPs such as seed and mulch or erosion mat.

DETAILED DESCRIPTION OF THE INVENTION

In an embodiment, a cross-linked polyacrylamide is added to the solid carrier which is then applied to the soil. Water is then applied to the solid carrier which releases the cross-linked polyacrylamide from the solid carrier into the soil. Superabsorbent cross-linked polyacrylamide are used in several types of applications for absorbing aqueous solutions. The polymers can be used for solidifying any water based material. These polymers act as a reservoir of water that is available to plants on demand, reducing plant shock and the effects of drought. When added to soil, plant roots grow directly into the water-swollen polymers, tapping the reserve as needed. An example of such a polymer includes a cross-linked potassium polyacrylate/polyacrylamide copolymer.

In an embodiment, a soil stabilizer is added to a solid carrier which is then applied to the soil. Water is applied to the solid carrier which then releases the soil stabilizer out of the solid carrier into the soil. Examples of soil stabilizers are: start xanthate, acid hydrolyzed cellulose microfibrils, chitin, gypsum, PAM, hydrocolloidal polysaccharide, acrylic copolymers, and/or sodium acrylate, and any combination of the above. Three polysaccharides (start xanthate, acid hydrolyzed cellulose microfibrils and chitin) have been shown to reduce soil loss. Polysaccharides are long chains of monosaccharides linked by glycosidic bonds. Three important polysaccharides, starch, glycogen and cellulose are composed of glucose. Starch and glycogen serve as short term energy stores in plants and animals, respectively. The glucose monomers are linked by glycosidic bonds. These are biodegradable polymers that have similar properties to water soluble PAM. In an embodiment of the present invention these polysaccharides are used as an additive or substitute to PAM.

Gypsum when combined with PAM is effective in reducing both soil loss and water runoff. Overall results indicate that a timely combination of these surface treatments such as tillage, mulch, canopy, gypsum, and PAM are useful and effective in combating water runoff and soil loss on cultivated lands. In an embodiment of the present invention, gypsum is used as an additive to the PAM of the present invention.

Guar gum is a natural high molecular weight hydrocolloidal polysaccharide composed of galactan and mannan units combined through glycosidic linkages which may be described chemically as galactomannan. It has been commonly used as a soil stabilizer for many years. It is a white to yellowish white powder. It is dissolved in cold or hot water, and forms a slime of high viscosity. In an embodiment of the present invention guar gum is used as an additive or a substitute for the PAM of the present invention.

Acrylic copolymers are commonly used as soil stabilizers. In addition, sodium acrylate is commonly combined with water soluble PAM and used as a soil stabilizer. An acrylate is a salt or ester of propenoic acid. In an embodiment of the present invention these are used as additives or substitutes of PAM.

In an embodiment, soil stabilizer is added to the solid carrier, wherein the solid carrier is comprised of at least about 25% particles in excess of 1 mm in diameter. The solid carrier is applied to the soil. Water is then applied to the solid carrier which releases the soil stabilizer out of the solid carrier into the soil. When dealing with polymers and fertilizers, soil amendments, soil mulches, and carriers, particle size matters as it affects agronomic response, granulation and process performance, and blending, storage, handling and application properties. In general, the smaller the particle size, the more rapidly dissolution occurs. Before about 1950, almost all fertilizers were produced as relatively fine powders or small crystals. As a result, fertilizers usually were dusty during handling and very susceptible to hard caking during storage in piles or bags. The growth of granulation (agglomeration) resulted in great improvement in storage, handling and application properties. This growth was paralleled by improvement in application equipment that took advantage of the better flow properties and reduction of caking in granular products. In the United States, the typical size range of granular fertilizer products is around 1-3.35 mm. In European countries and Japan, sizes are generally in the 2-4 mm range. In a preferred embodiment, the solid carrier is in the size range of about 5/16 to about 30 mesh (0.0234 inches or 600 microns).

In one embodiment of the invention the solid carrier is a mulch made by using a paper fiber based product, which can be moist, and impregnating it with PAM. In a further embodiment, the mulch can also be impregnated with soil amendments and fortifiers. A mixer can be used to create the mulch, preferably a pin mixer, but can also be a pan pelletizer, paddle mixer, drum granulator or other type of mixer. The paper fiber based product is preferably comprised of a by-product of a paper making process. Sewage sludge can be used to create the fortified mulch rather than paper fibers.

Below is an example of how a solid carrier (seed establishment mulch) of the present invention can be made using a pin mixer.

EXAMPLE

Pin Mixer:

In a pin mixer, agglomeration occurs, when radially extended pins mounted on a high velocity central rotor shaft, in a stationary cylindrical shell impart agitation forces on the material and sprayed liquid binder. This causes a tumbling movement resulting in densification.

Pin Arrangement:

Several different types of pin mixers were tested to determine the best pin arrangement for creating a mulch. The double helix pin arrangement resulted in a round more uniform pellet. The internal casing length and diameter were 23 inches and 6 inches, respectively. The dimensions of the shaft and pins included 2-inch diameter shaft and two-inch length pins. It was concluded that varying the speed (RPM) effected the pellet size. Increasing the speed caused a decrease in particle size. It was found that the pin mixer when set at 650 RPM resulted in a product that consisted largely of end-size (−6, +16) product. The material created a shell, but its amperage did not increase. Mulch through the pin mixer readily agglomerated and the discharged product was uniform in size and shape.

Retention Time:

A test was conducted to determine the retention time of the mulch. Material began to discharge at 2 seconds and ended at 23 seconds. The majority of the material took 8 seconds. Small particles had short retention time while larger particles took longer.

Pin Mixer: Material Feed Rates
Ground Wet Paper:

Wet paper was added at 33 lbs/hr, but the product was not uniform and round, so the feed was decreased to 200 lbs./hr. A uniform product was achieved at this rate. It was preferable to use a rate of 200 lbs/hr, however, a rate between 200 and 300 lbs/hr is also acceptable. The wet paper bridged in the screw feeder. The 3" feeder was the most consistent.

PAM:

PAM was added at a dry granular rate of 6 lbs/hr into the pin mixer. A uniform product was received at this rate with the PAM being successfully impregnated into the mulch granules.

Water:

An added 36-lbs/hr of water was metered into the pin mixer. The percent moisture in the paper was 52.3% water. A total of 140.6 lbs/hr of moisture is introduced when 200 lbs/hr of wet sludge is metered into the pin mixer.

NPK:

Nitrogen Phosphorous Potassium fortifiers was added to the pin at a rate of 28 lbs/hr. A vibratory feeder was required to feed such a low rate. The fertilizer had to be screened prior to addition into the feed hopper.

Coating Drum Wet Mulch Pellets:

The wet mulch pellets were hand fed into a rotary drum. The drum had no apparent problem with varied low or high feed rate. The rotary dryer placed limitations onto the coating drum feed rate. The majority (>90%) of agglomeration is done in the pin mixer. Since the material sent into the coating drum was in the form of a pellet, the material readily rolled.

Dryer:

The inlet and outlet air temperatures were 100 degrees Fahrenheit and 180 F, respectively. The sample at these settings had a material outlet temperature ranging from 150 to 175 degrees Fahrenheit and moisture content of 2.5%.

Sieve Analysis:

A sieve analysis was conducted with the use of a screen. The end-size portion was between 6 and 16 mesh. A three hour continuous run was produced, dried, and screened. The results concluded a total of 300 lbs of material; 206 lbs on size (68.7%), 53 lbs, under-size (17.7%), and 41 lbs, over-size (13.7%).

Mulch was applied with a conventional spreader. The desired application rate was set and achieved at a 1½ inch opening. The product was applied at a rate of 50 lbs/1,000 sq. ft. which was the desired application rate.

EXAMPLE 2

A laboratory test was conducted to impregnate a fertilizer granule (DAP) with PAM at a rate of 43 to 1. The raw materials were precisely measured and fed into an ammoniator-granulator along with the metered dry PAM particles. The granulator successfully agglomerated the finished solid carrier. The solid carrier was then dried and screened to size. The solid carrier was then metered to the turf stand with a conventional drop spreader. After watering the solid carrier successfully delivered the precise amount of nutrient and PAM to the turf stand.

What is claimed is:

1. A control product that binds soil particles together:
  said control product comprising a solid carrier and a water-soluble soil stabilizer (WSSS) soil amendment to bind said soil particles together;
  said WSSS is impregnated within said control product, applied onto said control product, or any combination thereof;
  an intentional amount of said WSSS leaches out from said control product into said soil;
  said intentional amount of WSSS that leaches out of said control product binds said soil particles together.

2. The control product of claim 1 further comprising nutrients wherein:
  said intentional amount of WSSS that leaches out of said control product binds said nutrients within said soil to reduce runoff of said nutrient from said soil, leaching of said nutrient from said soil, or any combination thereof.

3. The control product of claim 2 wherein said nutrients comprise calcium, magnesium, or any combination thereof.

4. The control product of claim 2 wherein said nutrients comprise iron, sulfur, manganese, boron, copper, zinc, molybdenum, nitrogen, phosphorus, potassium, or any combination thereof.

5. The control product of claim 1 further comprising an herbicide wherein:
  said intentional amount of WSSS that leaches out of said control product binds said herbicide within said soil to reduce runoff of said herbicide from said soil, leaching of said herbicide from said soil, or any combination thereof.

6. The control product of claim 1 further comprising a pesticide wherein:
  said intentional amount of WSSS that leaches out of said control product binds said pesticide within said soil to reduce runoff of said pesticide from said soil, leaching of said pesticide from said soil, or any combination thereof.

7. The control product of claim 6 wherein said pesticide is an insecticide.

8. A control product of claim 1 further comprising a microbe wherein:
  said intentional amount of WSSS that leaches out of said control product binds said microbe within said soil to reduce runoff of said microbe from said soil, leaching of said microbe from said soil, or any combination thereof.

9. The control product of claim 1 wherein said WSSS is an anionic water-soluble polyacrylamide (WSPAM).

10. The control product of claim 1 wherein said control product reduces erosion of said soil.

11. The control product of claim 1 wherein said solid carrier further comprises gypsum, a mineral, a soil amendment, a soil conditioner, a waste product, or any combination thereof.

12. The control product of claim 1 wherein said WSSS comprises a water-soluble polyacrylamide, start xanthate, acid hydrolyzed cellulose microfibrils, chitin, gypsum, hydrocolloidal polysaccharide, starch, glycogen and cellulose, acrylic copolymers, sodium acrylate, guar gum, polyethylene-imines, polyamides-amines, polyamines, polyethylene-oxide, sulfonated compounds, or any combination thereof.

13. The control product of claim 1 wherein
  said intentional amount of WSSS that leaches out of said control product binds said soil particles together to increase infiltration of water into said soil.

14. The control product of claim 2 wherein said nutrient is iron; said control product further comprises calcium and sulfur; said control product is an agglomerate; said agglomerate is formed by an agglomeration process; said agglomeration process is an agitation agglomeration process, pressure agglomeration process, or any combination thereof.

15. The control product of claim 1 wherein
said intentional amount of WSSS that leaches out of said control product binds said soil particles together to reduce time for seed emergence within said soil, reduce soil borne diseases within said soil, improve survival and growth of plants, improve root growth of plants within said soil, improve crop yield within said soil, expedite crop maturity within said soil, deepens plant rooting in said soil;
increases germination rates of seed in said soil, increases viability of shrub, tree, and/or vegetable transplants in said soil, or any combination thereof.

16. The control product of claim 15 wherein said control product further comprises a seed.

17. The control product of claim 15 wherein said control product further comprises a nutrient; said nutrient consisting of nitrogen, potassium, phosphorus, calcium, magnesium, iron, sulfur, manganese, boron, copper, zinc, molybdenum, or any combination thereof.

18. The control product of claim 10 wherein said solid carrier is an agglomerated mulch product.

* * * * *